US00PP28876P2

(12) United States Plant Patent
Davasse

(10) Patent No.: US PP28,876 P2
(45) Date of Patent: Jan. 16, 2018

(54) ***SPIRAEA* PLANT NAMED 'MATGOLD'**

(50) Latin Name: ***Spiraea* hybrid**
Varietal Denomination: Matgold

(71) Applicant: Van Belle Nursery, Abbotsford (CA)

(72) Inventor: Jean-Paul Davasse, Angers (FR)

(73) Assignee: VAN BELLE NURSERY, Abbortsford (CA)

( * ) Notice: Subject to any disclaimer, the term of this patent is extended or adjusted under 35 U.S.C. 154(b) by 0 days.

(21) Appl. No.: 15/330,206

(22) Filed: Aug. 22, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Penny J. Aguirre

(57) ABSTRACT

A new cultivar of *Spiraea* named 'Matgold' that is characterized by compact plant habit, its leaves that are copper red in color when young, changing to lemon gold in summer and changing to copper red in fall, and its flowers that open reddish pink in color and change to pink.

3 Drawing Sheets

Botanical classification: *Spiraea* hybrid.
Variety denomination: 'Matgold'.

CROSS, REFERENCE TO A RELATED APPLICATION

This application is related to a Canadian plant breeders' rights application filed on Jul. 27, 2015, application No. 15-8700. There have been no offers for sale anywhere in the world more than one year prior to the filing of this Application and no accessibility to one of ordinary skill in the art could have been derived from the printed plant breeder's rights documents.

BACKGROUND OF THE INVENTION

The present invention relates to a new and distinct cultivar of *Spiraea* of hybrid origin will be referred to hereafter by its cultivar name, 'Matgold'. 'Matgold' is a new variety of *Spiraea* grown for landscape use.

The new cultivar is the result of a controlled breeding program conducted by the Inventor in Angers, France with the goal of developing a new cultivar of *Spiraea* that exhibits young foliage that is copper red in color combined with deep pink-red flowers.

The new cultivar arose from a cross made by the Inventor in Angers, France in July of 2009 between *Spiraea japonica* 'Bailcarol' (not patented), as the female parent and *Spiraea*× *bumalda* 'Denistar' (U.S. Plant Pat. No. 22,432) as the male parent. The Inventor selected 'Matgold' as a single unique plant amongst the seedlings that resulted from the above cross in July of 2012.

Asexual propagation of the new cultivar was first accomplished by the Inventor by softwood stem cuttings in July of 2012 in Angers, France. Asexual propagation of the new cultivar by softwood stem cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Matgold' as a new and unique cultivar of *Spiraea*.

1. 'Matgold' exhibits a compact plant habit.
2. 'Matgold' exhibits leaves that are copper red in color when young, changing to lemon gold in summer and changing to copper red in fall.
3. 'Matgold' exhibits flowers that open reddish pink in color and change to pink.

The female parent of 'Matgold', 'Bailcarol' is similar to 'Matgold' in having a round plant habit and leaves that are small in size. 'Bailcarol' differs from 'Matgold' in having young leaves that are yellow in color and flowers that are light pink (without red) in color. The male parent of 'Matgold', 'Denistar', differs from 'Matgold' in having a more upright plant habit, leaves that are larger in size and emerge red then change to dark green in color and in having flowers that bloom red then turn reddish pink in color. 'Matgold' can also be most closely compared to the *Spiraea japonica* cultivar 'Goldflame' (not patented). 'Goldflame' is similar to 'Matgold' in having copper colored young foliage. 'Goldflame' differs from 'Matgold' in having a less compact plant habit and in having young foliage that is lighter red in color.

BRIEF DESCRIPTION OF THE DRAWINGS

The accompanying colored photographs illustrate the overall appearance and distinct characteristics of the new *Spiraea*. The photographs were taken of a plant two years in age as grown outdoors in a two-gallon container in St. Thomas, Ontario, Canada.

The photograph in FIG. 1 provides a view of the overall plant habit of 'Matgold' in bloom.

Figure 1:
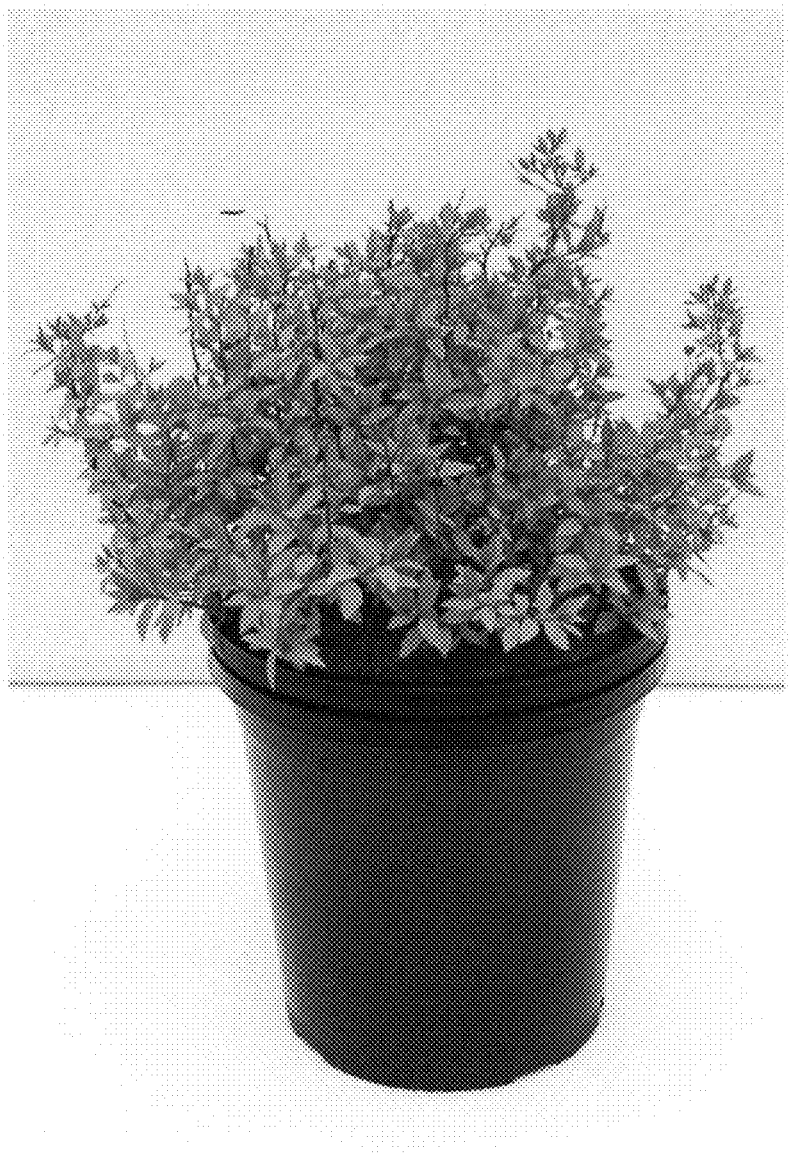
Figure 2:
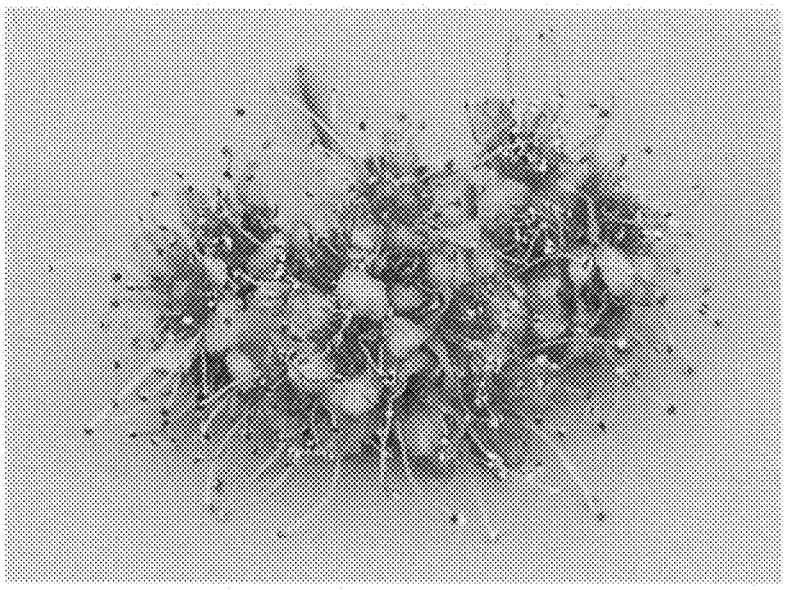

The photograph in FIG. 2 provides a close-up view of an inflorescence of 'Matgold'.

Figure 3:
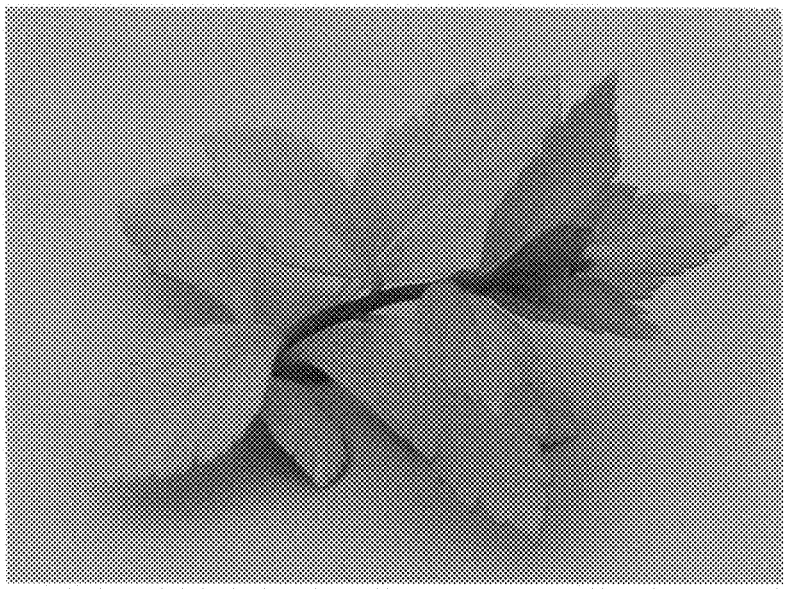

The photograph in FIG. 3 provides a close-up view of the young foliage of 'Matgold'.

Figure 4:
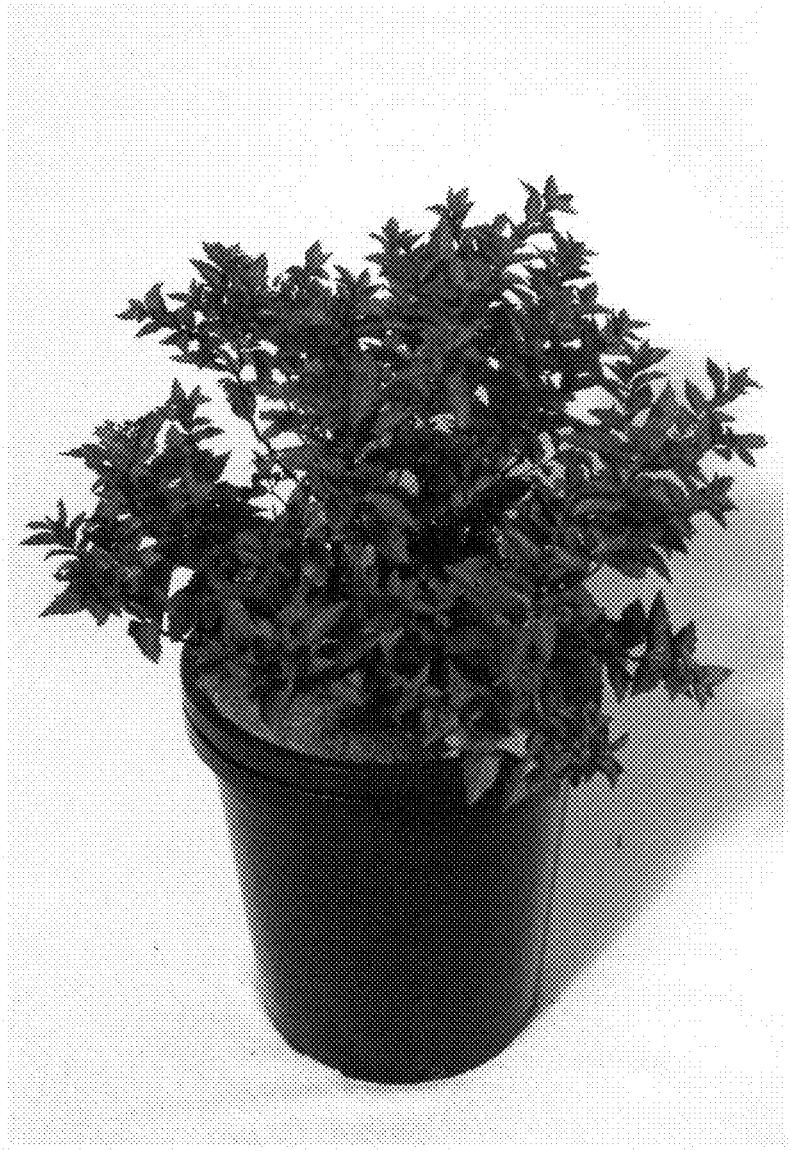

The photograph in FIG. 4 provides a view of the fall color.

The colors in the photographs are as close as possible with the digital photography techniques available, the color values cited in the detailed botanical description accurately describe the colors of the new *Spiraea*.

DETAILED BOTANICAL DESCRIPTION

The following is a detailed description of two year-old plants of the new cultivar as grown outdoors in two-gallon containers in St. Thomas, Ontario, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Initially blooms in May followed by a second bloom period in August in Ontario, Canada.

*Plant type*.—Deciduous shrub.

*Plant habit*.—Compact, mounded.

*Height and spread*.—Reaches an average of 40 cm in height and 65 cm in width.

*Hardiness*.—At least in U.S.D.A. Zones 3 to 8.

*Diseases*.—No unique susceptibility or resistance to diseases has been observed.

*Root description*.—Fibrous and fine.

*Propagation*.—Softwood stem cuttings.

*Growth rate*.—Moderate.

*Root initiation*.—Average of 7 to 10 days.

*Root development*.—Average of 120 days to fully develop in a 5-gallon container.

Branch description:

*Branch shape*.—Rounded.

*Branch color*.—New growth; 45D in spring and becoming 145C suffused with 184D in summer, mature wood; a blend of 177A and 199B.

*Branch size*.—Main branches; an average of 25 cm in length and 4 mm in width, lateral branches; an average of 15 cm in length and 1.8 mm in width.

*Branch strength*.—Strong.

*Branch surface*.—New growth; shiny and smooth, mature wood; bark-like but fairly smooth.

*Internode length*.—An average of 1 cm.

*Branching*.—An average of 25 main stems, an average of 10 lateral branches per main stem, stems held upright to an angle ranging between 35° (middle area) to 45° (outer area) to the main stem.

Foliage description:

*Leaf shape*.—Elliptic.

*Leaf division*.—Simple.

*Leaf base*.—Acute.

*Leaf apex*.—Acute.

*Leaf fragrance*.—None.

*Leaf venation*.—Pinnate, color of upper and lower surface on young unexpanded leaves is 180C, color of upper surface on mature leaves is 145B to 145C, color of lower surface on mature leaves is 145C.

*Leaf margins*.—Serrated.

*Leaf arrangement*.—Alternate.

*Leaf attachment*.—Petiolate.

*Leaf surface*.—Upper surface; glabrous and satiny, lower surface; glabrous and dull.

*Leaf size*.—Average of 4 cm in length and 2 cm in width.

*Leaf quantity*.—Average of 20 on a branch 15 cm in length.

*Leaf color*.—Spring; young upper and lower surface 180B to 180C, as leaves expand developing to 163B, mature upper surface N144C to N144D, mature lower surface N144D, summer; young and mature upper surface; 144A, young and mature lower surface; 138C, fall upper surface; 180A to 180B, and 179A, fall lower surface; 138B suffused with 180A especially at the margins.

*Petioles*.—Up to 4 mm in length and 0.6 mm in width, spring and summer color; 145C suffused with 180D at the margins, fall color; 138C and suffused with 180B, glabrous and satiny surface.

*Stipules*.—Glandular-like, an average of 2 mm in length and 1 mm in diameter, dull, flaky surface, 164B in color with 184C at apex.

Inflorescence description:

*Inflorescence type*.—Dense umbellate corymbs, present at terminus of lateral branches.

*Inflorescence size*.—Average of 4 cm in diameter and 2 cm in depth.

*Peduncles*.—Average of 1.5 cm in length and 0.4 mm in width, 146D in color suffused with 178B, glabrous surface, strong.

*Pedicels*.—An average of 2 mm in length and 0.3 mm in width, 146D in color suffused with 178B, glabrous surface, strong.

*Flower buds*.—Globose in shape, 1.3 mm in depth and diameter, 183B in color.

*Flower fragrance*.—None.

*Persistence of flowers*.—Calyx persistent.

*Flower quantity*.—Average of 60 per inflorescence.

*Lastingness of flowers*.—Each inflorescence lasts an average of 10 days with individual flowers lasting an average of 2 days.

*Flower type*.—Rotate with numerous extended stamens.

*Flower aspect*.—Inflorescence held upright on stem terminus.

*Flower size*.—Average of 6 mm in diameter and 3 mm in depth.

*Petals*.—5, average of 2 mm in length and width, un-fused, orbicular in shape, rounded base and apex, both surfaces glabrous, close to 64B in color when opening, when fully open 70A to 70B, not persistent.

*Calyx*.—Cone-shaped with flared tips, average of 3 mm in width and 2 mm in depth.

*Sepals*.—5, tips are an average of 1.3 mm in width and 1 mm in depth, fused base, ovate in shape, entire margins with fine hairs, acute apex, 146D suffused with 178B in color, surface glabrous on both surfaces except for margins.

Reproductive organs:

*Pistils*.—5, style; 2 mm in length and N57B in color, stigmas; 0.5 mm in diameter, 59C in color, ovaries; superior, oblong in shape, 0.8 mm in length and 0.4 mm in width, 155A suffused with N57B.

*Stamens*.—Average of 15, showy filaments; up to 6 mm in length and N80C in color, anthers; 0.3 mm in diameter, N79D in color, pollen; moderate in quantity, NN155B in color.

*Fruit and seed*.—None observed.

It is claimed:

1. A new and distinct cultivar of *Spiraea* plant named 'Matgold' as herein illustrated and described.

* * * * *